(12) United States Patent
Belliotti et al.

(10) Patent No.: US 6,177,422 B1
(45) Date of Patent: *Jan. 23, 2001

(54) BENZOXAZINONE DOPAMINE D4 RECEPTOR ANTAGONISTS

(75) Inventors: Thomas R. Belliotti, Saline; Lawrence D. Wise; David J. Wustrow, both of Ann Arbor, all of MI (US)

(73) Assignee: Warner-Lambert Company, Morris Plains, NJ (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/180,376

(22) PCT Filed: May 20, 1997

(86) PCT No.: PCT/US97/08524

§ 371 Date: Nov. 4, 1998

§ 102(e) Date: Nov. 4, 1998

(87) PCT Pub. No.: WO97/45419

PCT Pub. Date: Dec. 4, 1997

Related U.S. Application Data

(60) Provisional application No. 60/018,383, filed on May 29, 1996.

(51) Int. Cl.[7] .................... A61K 31/535; C07D 241/00; C07D 265/34
(52) U.S. Cl. .................... 514/230.5; 514/228.8; 544/105; 544/336; 544/98
(58) Field of Search ............ 544/105, 98, 336; 514/230.5, 228.8

(56) References Cited

U.S. PATENT DOCUMENTS

| | | | |
|---|---|---|---|
| 3,770,734 | 11/1973 | Pesson et al. | 260/244 |
| 5,196,434 | 3/1993 | Taverne et al. | 514/278 |
| 5,225,409 * | 7/1993 | Taverne et al. | 514/230.5 |
| 5,234,924 | 8/1993 | Taverne et al. | 514/224.2 |
| 5,240,919 | 8/1993 | Yous et al. | 514/210 |
| 5,268,381 | 12/1993 | Taverne et al. | 514/367 |
| 5,296,477 | 3/1994 | Taverne et al. | 514/224.2 |
| 5,300,507 | 4/1994 | Yous et al. | 514/253 |
| 5,322,843 | 6/1994 | Yous et al. | 514/233.8 |
| 5,322,849 | 6/1994 | Yous et al. | 514/321 |
| 5,326,775 | 7/1994 | Yous et al. | 514/375 |
| 5,386,034 | 1/1995 | Yous et al. | 548/169 |
| 5,436,348 | 7/1995 | Yous et al. | 548/221 |
| 5,919,784 * | 7/1999 | Lesieur et al. | 514/253 |

FOREIGN PATENT DOCUMENTS

| | | |
|---|---|---|
| 44403/97 | 5/1998 | (AU) . |
| 0154969A2 | 9/1985 | (EP) . |
| 0233728A1 | 8/1987 | (EP) . |
| 0478446A1 | 4/1992 | (EP) . |
| 0506539A1 | 9/1992 | (EP) . |
| 94/03426 | 2/1994 | (WO) . |
| 97/45419 | 12/1997 | (WO) . |

* cited by examiner

*Primary Examiner*—Richard L. Raymond
*Assistant Examiner*—Sudhaker B. Patel
(74) *Attorney, Agent, or Firm*—Todd M. Crissey; Michael J. Atkins; Charles W. Ashbrook

(57) ABSTRACT

This invention relates to compounds that are antagonists of dopamine D4 receptors, to methods of treating psychosis and schizophrenia using a compound that is an antagonist of dopamine D4 receptors, and to pharmaceutically acceptable compositions that contain a dopamine D4 receptor antagonist.

21 Claims, No Drawings

BENZOXAZINONE DOPAMINE D4 RECEPTOR ANTAGONISTS

This APPLICATION is a 371 of PCT/US97/08524 filed May 20, 1997. This application claims the benefit of Provisional Application 60/018,383 filed May 29, 1996.

FIELD OF THE INVENTION

This invention relates to compounds that are antagonists at dopamine D4 receptors, to methods of treating psychosis and schizophrenia using a compound that is an antagonist at dopamine D4 receptors, and to pharmaceutically acceptable compositions that contain a dopamine D4 receptor antagonist.

BACKGROUND OF THE INVENTION

Dopamine is a neurotransmitter that is found in the brains of animals, including humans, and is essential for proper nerve signal transmission. It is well-known that certain compounds block or inhibit the binding of dopamine to dopamine receptors. Such compounds are called dopamine receptor antagonists. It is also well-known that dopamine receptor antagonists are useful in the treatment of schizophrenia and psychosis.

Recently, it has been discovered that more than one type of dopamine receptor exists, and that dopamine receptor antagonists can preferentially inhibit one type of dopamine receptor over another. Two major families of dopamine receptors have been identified and named the D1 and D2 families. In the D2 family, three distinct receptor subtypes have been identified as D2, D3, and D4.

The distribution and concentration of the subtypes of receptors varies in different regions of the brain. D2 subtype receptors are located in both the limbic region of the brain, which is associated with cognition and emotional function, and in the striatum, which is associated with motor effects. D4 receptors are found in higher concentrations in the frontal cortex and limbic regions, which are associated with cognitive and emotional function.

Antipsychotic drugs that are D2 subtype receptor antagonists have been used to treat psychosis and schizophrenia, but have undesirable extrapyramidal side effects and produce tardive dyskinesia. In contrast, D4 receptor antagonists show a lack of extrapyramidal side effects and tardive dyskinesia. Moreover, it has been observed that the levels of dopamine D4 receptors are elevated in schizophrenics.

Thus, it would be useful to have compounds that are selective D4 antagonists for the treatment of psychosis and schizophrenia.

SUMMARY OF THE INVENTION

The present invention provides compounds of the Formulas I and II

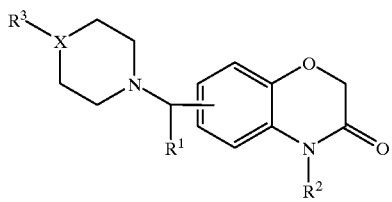

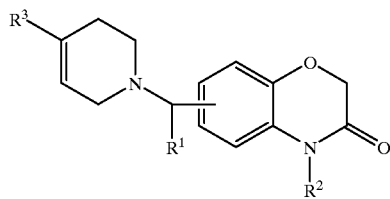

wherein $R^1$ and $R^2$ are independently hydrogen or $C_1$–$C_6$ alkyl;

X is N or CH; and $R^3$ is phenyl, naphthyl, heteroaryl, substituted phenyl, substituted naphthyl or substituted heteroaryl, wherein each substituent is independently selected from halogen, $C_1$–$C_6$ alkoxy, $C_1$–$C_6$ alkyl, —CN, —$CF_3$, or sulphonamido, and the pharmaceutically acceptable salts, esters, amides, and prodrugs thereof.

In a preferred embodiment of Formula I or II, the group

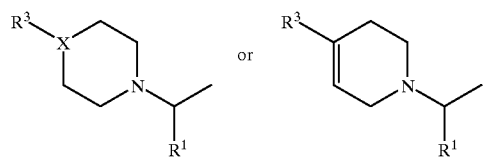

is attached to the benzoxazinone group at the 6 or 7 position.

In another preferred embodiment, $R^1$ and $R^2$ are hydrogen.

In another preferred embodiment, $R^3$ is phenyl, methyltolyl, tolyl, or sulfonamido.

In another preferred embodiment, X is N.

The present invention also provides compounds of Formula III,

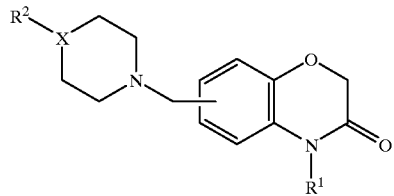

wherein X is N or CH; $R^1$ is hydrogen or methyl; and $R^2$ is phenyl or substituted phenyl wherein each substituent is independently selected from $C_1$–$C_6$ alkyl or sulphonamido, and the pharmaceutically acceptable salts, esters, amides, and prodrugs thereof.

In a preferred embodiment of Formula III, the group,

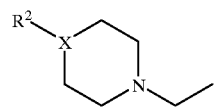

is attached to the benzoxazinone group at the 6 or 7 position.

In another preferred embodiment, $R^1$ is hydrogen.

In another preferred embodiment, $R^2$ is phenyl, methyltolyl, tolyl, or sulfonamido.

In a most preferred embodiment, the compounds of Formula I, II, and III are:

4-[4-(3-oxo-3,4-dihydro-2H-benzo[1,4]oxazin-6-ylmethyl)-piperazin-1-yl]-benzenesulfonamide;
6-[4-(3,4-dimethyl-phenyl)-piperazin-1-ylmethyl)]-4H-benzo[1,4]oxazin-3-one;
6-(4-p-tolyl-piperazin-1-ylmethyl)-4H-benzo[1,4]oxazin-3-one;
6-[4-phenyl-piperazin-1-ylmethyl]-4H-benzo[1,4]oxazin-3-one;
7-(4-p-tolyl-piperazin-1-ylmethyl)-4H-benzo[1,4]oxazin-3-one;
7-(4-phenyl-piperazin-1-ylmethyl)-4H-benzo[1,4]oxazine-3-one;
7-[4-(3,4-dimethyl-phenyl)-piperazin-1-ylmethyl]-4H-benzo[1,4]oxazine-3-one;
6-[4-(5-methyl-pyridin-2-yl)-piperazin-1-ylmethyl]-4H-benzo[1,4]oxazin-3-one;
6-(4-p-tolyl-piperidin-1-ylmethyl)-4H-benxo[1,4]oxazin-3-one;
6-[4-(3,4-Dimethyl-phenyl)-piperidin-1-ylmethyl]-4H-benzo[1,4]oxazin-3-one;
6-(4-thiazol-2-yl-piperazin-1-ylmethyl)-4H-benzo[1,4]oxazin-3-one;
6-(4-benzothiazol-2-yl-piperazin-1-ylmethyl)-4H-benzo[1,4]oxazin-3-one;
6-[4-(4,5-dimethyl-thiazol-2-yl)-piperazin-1-ylmethyl]-4H-benzo[1,4]oxazin-3-one;
6-(4-naphthalen-2-yl-piperazin-1-ylmethyl)-4H-benzo[1,4]oxazin-3-one;
6-[4-(3-chloro-phenyl)-piperazin-1-ylmethyl]-4H-benzo[1,4]oxazin-3-one;
6-[4-(3,4-dichloro-phenyl)-piperazin-1-ylmethyl]-4H-benzo[1,4]oxazin-3-one;
2-[4-(3-oxo-3,4-dihydro-2H-benzo[1,4]oxazin-6-ylmethyl)-piperazin-1-yl]-benzonitrile;
6-[4-(4-methoxy-phenyl)-piperazin-1-ylmethyl]-4H-benzo[1,4]oxazin-3-one;
6-[4-(2-chloro-4-methyl-phenyl)-piperazin-1-ylmethyl]-4H-benzo[1,4]oxazin-3-one;
6-[4-(4-Fluoro-phenyl)-piperazin-1-ylmethyl]-4H-benzo[1,4]oxazin-3-one;
6-[4-(3-Trifluoromethyl-phenyl)-piperazin-1-ylmethyl]-4H-benzo[1,4]oxazin-3-one;
6-[4-(3,5-Dimethyl-phenyl)-piperazin-1-ylmethyl]-4H-benzo[1,4]oxazin-3-one;
6-[4-(2-Chloro-phenyl)-piperazin-1-ylmethyl]-4H-benzo[1,4]oxazin-3-one;
6-[4-(4-Trifluoromethyl-phenyl)-piperazin-1-ylmethyl]-4H-benzo[1,4]oxazin-3-one;
6-[4-(4-Chloro-phenyl)-piperazin-1-ylmethyl]-4H-benzo[1,4]oxazin-3-one;
7-[4-(5-Methyl-pyridin-2-yl)-piperazin-1-ylmethyl]-4H-benzo[1,4]oxazin-3-one;
7-[4-(4-Methoxy-phenyl)-piperazin-1-ylmethyl]-4H-benzo[1,4]oxazin-3-one;
7-[4-(4-Chloro-phenyl)-piperazin-1-ylmethyl]-4H-benzo[1,4]oxazin-3-one;
7-[4-(3,4-Dimethyl-phenyl)-piperidin-1-ylmethyl]-4H-benzo[1,4]oxazin-3-one;
6-[4-(4-Methoxy-phenyl)-piperidin-1-ylmethyl]-4H-benzo[1,4]oxazin-3-one;
7-[4-(4-Methoxy-phenyl)-piperidin-1-ylmethyl]-4H-benzo[1,4]oxazin-3-one;
7-(4-Phenyl-piperidin-1-ylmethyl)-4H-benzo[1,4]oxazin-3-one;
7-(4-Naphthalen-2-yl-piperazin-1-ylmethyl)-4H-benzo[1,4]oxazin-3-one; or
7-(4-p-Tolyl-piperidin-1-ylmethyl)-4H-benzo[1,4]oxazin-3-one.

Also provided by the present invention is a method of treating psychosis, the method comprising administering to a patient suffering therefrom a therapeutically effective amount of a compound of Formula I, II, or III.

Also provided by the present invention is a method of treating schizophrenia, the method comprising administering to a patient suffering therefrom a therapeutically effective amount of a compound of Formula I, II, or III.

Also provided by the present invention is a pharmaceutically acceptable composition that comprises a compound of Formula I, II, or III.

DETAILED DESCRIPTION OF THE INVENTION

The present invention provides compounds of the Formulas I and II

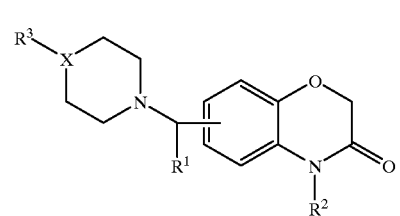

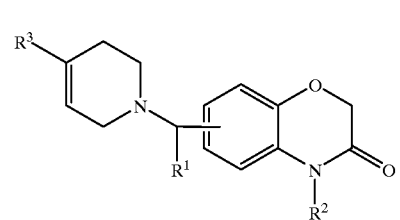

wherein $R^1$ and $R^2$ are independently hydrogen or $C_1$–$C_6$ alkyl;

X is N or CH; and $R^3$ is phenyl, naphthyl, heteroaryl, or substituted phenyl, substituted naphthyl or substituted heteroaryl wherein each substituent is independently selected from halogen, $C_1$–$C_6$ alkoxy, $C_1$–$C_6$ alkyl-CN, —$CF_3$, or sulphonamido, and the pharmaceutically acceptable salts, esters, amides, and prodrugs thereof. The term substituted phenyl included phenyl substituted with one or more substituent.

The present invention also provides compounds of Formula III,

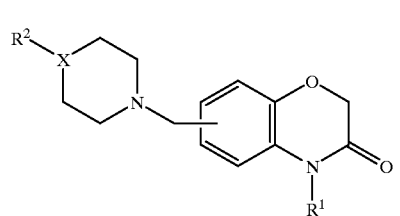

wherein X is N or CH; $R^1$ is hydrogen or methyl; and $R^2$ is phenyl or substituted phenyl, wherein each substituent is independently selected from $C_1$–$C_6$ alkyl or sulphonamido, and the pharmaceutically acceptable salts, esters, amides, and prodrugs thereof.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "aryl" means a cyclic aromatic hydrocarbon. Representative examples of aryl groups include phenyl and naphthyl, which can be substituted or unsubstituted. Examples of suitable substituents include halogen, $C_1$–$C_6$ alkyl, hydroxy, $C_1$–$C_6$ alkoxy, —$CF_3$, and sulfonamides.

The term "heteroaryl" means a cyclic hydrocarbon that contains one or more heteroatom. Representative examples of heteroaryl groups are thiazole, thiophene, and pyridine, pyrimidine, quinoline, isoquinoline, and imidazole. The heteroaryl group can be substituted or unsubstituted. Examples of suitable substituents include $C_1$–$C_6$ alkyl, $C_1$–$C_6$ alkoxy, or halogen.

The term "heteroatom" means an atom other than carbon. Examples of heteroatoms include nitrogen, oxygen, sulfur, and phosphorus.

The term "halogen" means chlorine, fluorine, bromine, and iodine.

The term "sulfonamido" means a group having the structure —$SO_2NR^aR^b$, where $R^a$ and $R^b$ are sulfonamido substituents well known to those in the art such as hydrogen and $C_1$–$C_6$ alkyl.

The symbol "—" means a bond.

The atoms in the benzoxazinone group can be numbered as shown below:

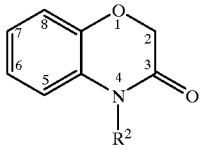

The term "patient" includes humans.

A "therapeutically effective amount" is an amount of a compound of the present invention that when administered to a patient ameliorates a symptom of psychosis or schizophrenia. A therapeutically effective amount of a compound of the present invention can be easily determined by one skilled in the art by administering a quantity of a compound to a patient and observing the result. In addition, those skilled in the art are familiar with identifying patients having psychosis and schizophrenia and are readily able to identify patients who suffer from psychosis and schizophrenia.

The term "pharmaceutically acceptable salts, esters, amides, and prodrugs" as used herein refers to is those carboxylate salts, amino acid addition salts, esters, amides, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," *J. Pharm. Sci.*, 1977;66:1–19 which is incorporated herein by reference).

Examples of pharmaceutically acceptable, nontoxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, nontoxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

The compounds of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft- and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable nonirritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 1,000 mg per day. For a normal human adult having a body weight of about 70 kg, a dosage in the range of about 0.01 to about 100 mg/kg of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well-known to those skilled in the art.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisometric forms by virtue of the presence of asymmetric centers in the compounds. It is contemplated that all stereoisometric forms of the compounds as well as mixtures thereof, including racemic mixtures, form part of this invention.

The examples shown below illustrate particular embodiments of the invention and are not intended to limit the specification, including the claims, in any manner.

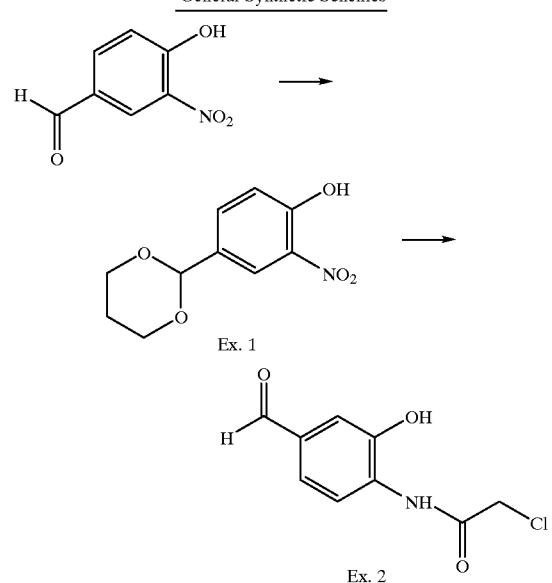

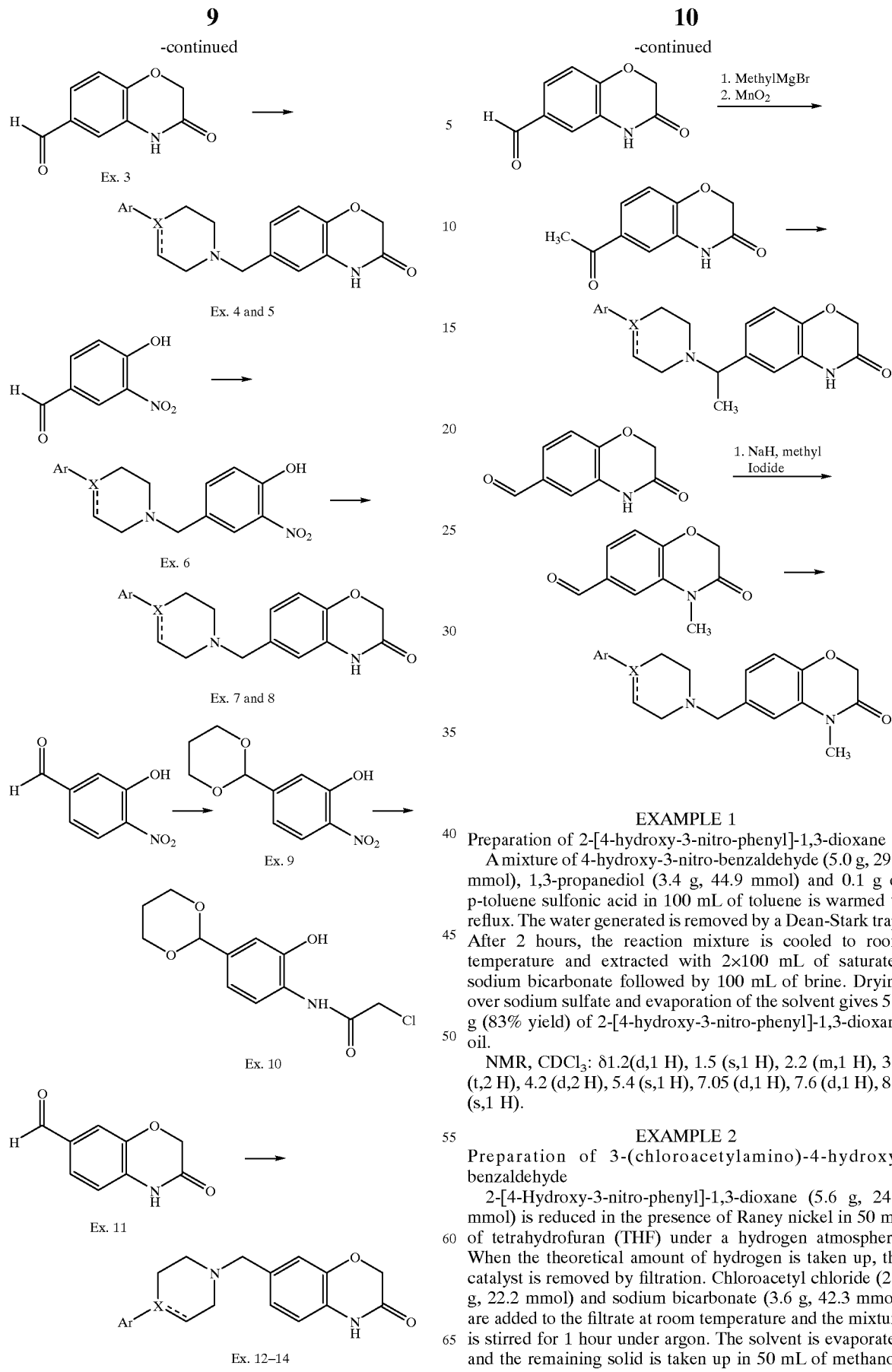

EXAMPLE 1

Preparation of 2-[4-hydroxy-3-nitro-phenyl]-1,3-dioxane

A mixture of 4-hydroxy-3-nitro-benzaldehyde (5.0 g, 29.9 mmol), 1,3-propanediol (3.4 g, 44.9 mmol) and 0.1 g of p-toluene sulfonic acid in 100 mL of toluene is warmed to reflux. The water generated is removed by a Dean-Stark trap. After 2 hours, the reaction mixture is cooled to room temperature and extracted with 2×100 mL of saturated sodium bicarbonate followed by 100 mL of brine. Drying over sodium sulfate and evaporation of the solvent gives 5.6 g (83% yield) of 2-[4-hydroxy-3-nitro-phenyl]-1,3-dioxane oil.

NMR, CDCl$_3$: δ1.2(d,1 H), 1.5 (s,1 H), 2.2 (m,1 H), 3.9 (t,2 H), 4.2 (d,2 H), 5.4 (s,1 H), 7.05 (d,1 H), 7.6 (d,1 H), 8.2 (s,1 H).

EXAMPLE 2

Preparation of 3-(chloroacetylamino)-4-hydroxy-benzaldehyde

2-[4-Hydroxy-3-nitro-phenyl]-1,3-dioxane (5.6 g, 24.9 mmol) is reduced in the presence of Raney nickel in 50 mL of tetrahydrofuran (THF) under a hydrogen atmosphere. When the theoretical amount of hydrogen is taken up, the catalyst is removed by filtration. Chloroacetyl chloride (2.5 g, 22.2 mmol) and sodium bicarbonate (3.6 g, 42.3 mmol) are added to the filtrate at room temperature and the mixture is stirred for 1 hour under argon. The solvent is evaporated and the remaining solid is taken up in 50 mL of methanol. The solution is acidified to a pH of about one with 1.0 N HCl and stirred at room temperature for 1 hour. The precipitate is collected and dried under vacuum to give 2.5 g (65% yield) of 3-(chloroacetylamino)-4-hydroxy-benzaldehyde as a hydrate; mp 190–192° C.

Analysis for $C_9H_8ClNO_3 \cdot 0.9\ H_2O$: C, 50.41; H, 4.18; N, 6.53.

Found: C, 50.60; H, 3.83; N, 6.41.

EXAMPLE 3
Preparation of 3-oxo-3,4-dihydro-2H-benzo[1,4]oxazine-6-carbaldehyde 3-(Chloroacetylamino)-4-hydroxy-benzaldehyde (2.4 g, 13.2 mmol) and potassium carbonate (9.1 g, 66.1 mmol) are stirred at room temperature in 50 mL of acetonitrile for 12 hours. The acetonitrile is evaporated and the residue is taken up in 50 mL of water. After standing at room temperature for 10 minutes, the precipitate is collected by filtration and recrystallized from ethyl acetate to give 1.4 g (60% yield) of 3-oxo-3,4-dihydro-2H-benzo[1,4]oxazine-6-carbaldehyde; mp 220–222° C.

Analysis for $C_9H_7NO_3$: C, 61.02; H, 3.98; N, 7.91.

Found: C, 60.67; H, 4.03; N, 7.74.

EXAMPLE 4
Preparation of 4-[4-(3-oxo-3,4-dihydro-2H-benzo[1,4]-oxazin-6-ylmethyl)-piperazin-1-yl]-benzenesulfonamide Sodium triacetoxyborohydride (1.2 g, 5.9 mmol) is added to a solution of 3-oxo-3,4-dihydro-2H-benzo[1,4]-oxazine-6-carbaldehyde (0.5 g, 2.8 mmol) and 4-(piperazin-1-yl)-benzenesulfonamide (0.17 g, 3.1 mmol) in 20 mL of THF. The mixture is stirred at room temperature overnight. The reaction is quenched by addition of 50 mL of water, and the THF is removed under reduced pressure. The precipitate is collected by filtration and recrystallized from methanol to give 0.05 g (4% yield) of 4-[4-(3-oxo-3,4-dihydro-2H-benzo[1,4]oxazin-6-ylmethyl)-piperazin-1-yl]-benzenesulfonamide; mp 150–153° C.

Analysis for $C_{19}H_{22}N_4O_4S$: C, 56.70; H, 5.51; N, 13.92; S, 7.97.

Found: C, 56.57; H, 5.56, N, 13.67; S, 7.80.

EXAMPLE 5
Preparation of 6-[4-(3,4-Dimethyl-phenyl)-piperazin-1-ylmethyl]-4H-benzo[1,4]oxazin-3-one 1-(3,4-Dimethylphenyl)-piperazine is converted to 6-[4-(3,4-dimethyl-phenyl)-piperazin-1-ylmethyl]-4H-benzo[1,4]oxazin-3-one in 10% yield according to the procedure of Example 4; mp 148–153° C.

Analysis for $C_{21}H_{25}N_3O_2$: C, 71.77; H, 7.17; N, 11.96.

Found: C, 71.50; H, 7.18; N, 11.92.

EXAMPLE 6
Preparation of 4-[4-(methylphenyl)-piperazin-1-ylmethyl]-2-nitro-phenol Sodium triacetoxyborohydride (1.8 g, 8.4 mmol) is added to a solution of 4-hydroxy-3-nitro-benzaldehyde (1.3 g, 8.0 mmol) and 1-(4-methyl-phenyl)-piperazine (2.8 g, 16.1 mmol) in 50 mL of THF at room temperature, and the mixture is stirred overnight. The reaction is quenched by pouring into 400 mL of water, and the precipitate which forms is collected by filtration. Yield=1.7 g (33%) of 4-[4-(methylphenyl)-piperazin-1-ylmethyl]-2-nitro-phenol oil.

NMR, $CDCl_3$: δ2.2 (s,3 H), 2.5 (m,4 H), 3.05 (m,4 H), 3.4 (s,2 H), 6.8 (d,2 H), 7.0 (d,2 H), 7.05 (d,1 H), 7.55 (d,1 H), 8.0 (s,1 H).

EXAMPLE 7
Preparation of 6-(4-p-tolyl-piperazin-1-ylmethyl)-4H-benzo[1,4]oxazine-3one 4-[4-(Methylphenyl)-piperazin-1-ylmethyl]-2-nitro-phenol (1.7 g, 5.2 mmol) is reduced with Raney nickel in 20 mL of THF under hydrogen. When the theoretical amount of hydrogen is taken up, the catalyst is removed by filtration. The THF is evaporated, and the residue is taken up in 50 mL of chloroform. Chloroacetyl chloride (0.65 g, 5.7 mmol) and sodium bicarbonate (1.6 g, 19.1 mmol) are added, and the mixture is stirred at room temperature for one-half hour, then extracted with water (3×50 mL) and dried over sodium sulfate. The solvent is evaporated, and the solid remaining is treated with excess potassium carbonate in 20 mL of chloroform at reflux overnight. Extraction with water, drying over sodium sulfate, and evaporation of the solvent gives a yellow solid. Recrystallization from ethyl acetate gives 0.27 g (16% yield) of 6-(4-p-tolyl-piperazin-1-ylmethyl)-4H-benzo[1,4]oxazin-3-one; mp 209–212° C.

Analysis for $C_{20}H_{23}N_3O_2$:

Calculated C, 71.19; H, 6.87; N, 12.45.

Found: C, 71.05; H, 6.97; N, 12.35.

EXAMPLE 8
Preparation of 6-[4-phenyl-piperazin-1-ylmethyl]-4H-benzo[1,4]oxazin-3-one 4-(4-Phenyl-piperazine-1-ylmethyl)-2-nitro-phenol is treated according to the procedure of Example 7 to give 6-[4-phenyl-piperazin-1-ylmethyl]-4H-benzo[1,4]-oxazin-3-one; mp 207–209° C.

EXAMPLE 9
Preparation of 2-(3-hydroxy-4-nitro-phenyl)-1,3-dioxane

3-Hydroxy-4-nitro-benzaldehyde (7.5 g, 44.9 mmol) is treated with 1,3-propanediol (5.1 g, 67.3 mmol) according to the procedure of Example 1 to give 2-(3-hydroxy-4-nitro-phenyl)-1,3-dioxane (9.6 g, 95% yield) oil.

NMR, $CDCl_3$: δ1.4 ($d_{,1}$ H), 7.05 (d,1 H), 2.2 (m,1 H), 3.9 (t,2 H), 4.2 (d,2 H), 5.4 (s,1 H), 7.2 (s,1 H), 8.0 (d,1 H).

EXAMPLE 10
Preparation of 4-(chloroacetyl-amino)-3-hydroxy-benzaldehyde 2-(3-Hydroxy-4-nitro-phenyl)-1,3-dioxane (9.3 g, 41.2 mmol) is converted to 4-(chloroacetyl-amino)-3-hydroxy-benzaldehyde according to the procedure of Example 2. Yield=3.7 g (35%) oil.

NMR, DMSO: δ4.4 (s,1 H), 7.3 (s,1 H), 7.4 (d,1 H), 8.2 (d,1 H), 9.7 ($s_{,1}$ 1H), 9.8 (s,1 H), 10.7 (s,1 H).

EXAMPLE 11
Preparation of 3-oxo-dihydro-2H-benzo[1,4]oxazine-7-carbaldehyde 4-(Chloroacetyl-amino)-3-hydroxy-benzaldehyde (3.7 g, 17.3 mmol) is converted to 3-oxo-3,4-dihydro-2H-benzo[1,4]oxazine-7-carbaldehyde (3.2 g, 100% yield) according to the procedure of Example 3; mp 178–180° C. (Decomposes).

EXAMPLE 12
Preparation of 7-(4-p-Tolyl)-piperazin-1-ylmethyl)-4H-benzo[1,4]oxazin-3-one A mixture of 3-oxo-dihydro-2H-benzo[1,4]oxazine-7-carbaldehyde (0.5 g, 2.8 mmol), 1-(4-methyl-phenyl)-piperazine (0.5 g, 2.8 mmol), acetic acid (0.17 g, 2.8 mmol) and sodium triacetoxyborohydride (1.2 g, 5.9 mmol) in 20 mL of 1,2-dichloroethane is stirred at room temperature for 3 hours. The reaction is quenched with 50 mL of water, and the layers are separated. The aqueous phase is extracted with ethyl acetate (3×50 mL). The organic phases are combined and dried over sodium sulfate. Evaporation of the solvent gives a solid which is recrystallized twice from acetonitrile to give 0.31 g (33% yield) of 7-[4-(4-methyl-phenyl)-piperazin-1-ylmethyl]-4H-benzo[1,4]oxazine-3-one; mp 208–210° C.

Analysis for $C_{20}H_{23}N_3O_2$: C, 71.19; H, 6.87; N, 12.45. Found: C, 71.10; H, 6.73; N, 12.32.

EXAMPLE 13
Preparation of 7-(4-phenyl-piperazin-1-ylmethyl)-4H-benzo[1,4]oxazine-3-one 1-Phenyl-piperazine (0.45, 2.8 mmol) is converted to 7-(4-phenyl-piperazin-1-ylmethyl)-4H-benzo[1,4]-oxazine-3-one according to the procedure of Example 12 in 34% yield; mp 191–193° C.

EXAMPLE 14
Preparation of 7-[4-(3,4,-dimethyl-phenyl)-piperazin-1-ylmethyl]-4H-benzo[1,4]oxazine-3-one According to the procedure of Example 12, 1-(3,4-dimethyl-phenyl)-piperazine (0.54 g, 2.8 mmol) is converted to 7-[4-(3,4-dimethyl-phenyl)-piperazin-1-ylmethyl]-4H-benzo[1,4]oxazine-3-one in 28% yield; mp 195–197° C.

The compounds listed below can be prepared in accordance with the above methods using the appropriate starting materials.

| Example Number | Compound Name | Elemental Analysis | Melting Point ° C. |
|---|---|---|---|
| 15 | 6-[4-(5-Methyl-pyridin-2-yl)-piperazin-1-ylmethyl]-4H-benzo[1,4]oxazin-3-one | $C_{19}H_{22}N_4O_2$ Calculated: C, 67.44; H, 6.55; N, 16.56 Found: C, 67.35; H, 6.53; N, 16.58 | 207–208 |
| 16 | 6-(4-p-Tolyl-piperidin-1-ylmethyl)-4H-benzo[1,4]oxazin-3-one | $C_{21}H_{24}N_2O_2$ Calculated: C, 74.96; H, 7.20; N, 8.33 Found: C, 74.73; H, 7.30; N, 8.36 | 178–180 |
| 17 | 6-[4-(3,4-Dimethyl-phenyl)-piperidin-1-ylmethyl]-4H-benzo[1,4]oxazin-3-one | $C_{22}H_{26}N_2O_2$ Calculated: C, 75.40; H, 7.48; N, 7.99 Found: C, 75.39; H, 7.62; N, 8.10 | 165–169 |
| 18 | 6-(4-thiazol-2-yl-piperazin-1-ylmethyl)-4H-benzo[1,4]oxazin-3-one | $C_{16}H_{18}N_4O_2S$ Calculated: C, 58.16; H, 5.49; N, 16.96 Found: C, 58.32; H, 5.59; N, 17.03 | 210–212 |
| 19 | 6-(4-Benzothiazol-2-yl-piperazin-1-ylmethyl)-4H-benzo[1,4]oxazin-3-one | $C_{20}H_{20}N_4O_2S$ Calculated: C, 63.14; H, 5.30; N, 14.73 Found: C, 62.72; H, 5.24; N, 14.45 | 240–243 |
| 20 | 6-[4-(4,5-dimethyl-thiazol-2-yl)-piperazin-1-ylmethyl]-4H-benzo[1,4]oxazin-3-one | $C_{18}H_{22}N_4O_2S$ Calculated: C, 60.31; H, 6.19; N, 15.63; S, 8.94 Found: C, 60.31; H, 6.11; N, 15.56; S, 9.21 | 210–212 |
| 21 | 6-(4-Naphthalen-2-yl-piperazin-1-ylmethyl)-4H-benzo[1,4]oxazin-3-one | $C_{23}H_{23}N_3O_2$ Calculated: C, 73.97; H, 6.21; N, 11.25 Found: C, 73.70; H, 6.21; N, 10.90 | 215–216 |
| 22 | 6-[4-(3-Chloro-phenyl)-piperazin-1-ylmethyl]-4H-benzo[1,4]oxazin-3-one | $C_{19}H_{20}ClN_3O_2$ Calculated: C, 63.77; H, 5.63; N, 11.74 Found: C, 63.78; H, 5.50; N, 11.54 | 199–200 |
| 23 | 6-[4-(3,4-Dichloro-phenyl)-piperazin-1-ylmethyl]-4H-benzo[1,4]oxazin-3-one | $C_{19}H_{19}C_{12}N_3O_2$ Calculated: C, 58.17; H, 4.88; N, 10.71 Found: C, 58.30; H, 4.77; N, 10.43 | 174–175 |
| 24 | 2-[4-(3-Oxo-3,4-dihydro-2H-benzo[1,4]oxazin-6-ylmethyl)-piperazin-1-yl]-benzonitrile | $C_{20}H_{20}N_4O_2$ Calculated: C, 68.95; H, 5.79; N, 16.08 Found: C, 68.91; H, 5.78; N, 15.93 | 195–196 |
| 25 | 6-[4-(4-Methoxy-phenyl)-piperazin-1-ylmethyl]-4H-benzo[1,4]oxazin-3-one | $C_{20}H_{23}N_3O_3$ Calculated: C, 67.97; H, 6.56; N, 11.80 Found: C, 67.87; H, 6.56, N, 11.72 | 202–203 |
| 26 | 6-[4-(2-Chloro-4-methyl-phenyl)-piperazin-1-ylmethyl]-4H-benzo[1,4]oxazin-3-one | $C_{20}H_{22}ClN_3O_2$ Calculated: C, 64.60; H, 5.96; N, 11.30; Cl, 9.53 Found: C, 64.21; H, 5.79; N, 11.01; Cl, 9.47 | 188–189 |
| 27 | 6-[4-(4-Fluoro-phenyl)-piperazin-1-ylmethyl]-4H-benzo[1,4]oxazin-3-one | $C_{19}H_{20}FN_3O_2$ Calculated: C, 66.85; H, 5.91; N, 12.31 Found: C, 66.56; H, 5.88, N, 12.12 | 226–227 |
| 28 | 6-[4-(3-Trifluoromethyl-phenyl)-piperazin-1-ylmethyl]-4H-benzo[1,4]oxazin-3-one | $C_{20}H_{20}F_3N_3O_2$ Calculated: C, 61.38; H, 5.15; N, 10.74 Found: C, 61.29; H, 5.12; N, 10.64 | 191–192 |
| 29 | 6-[4-(3,5-Dimethyl-phenyl)-piperazin-1-ylmethyl]-4H-benzo[1,4]oxazin-3-one | $C_{21}H_{25}N_3O_2$ Calculated: C, 71.77; H, 7.17; N, 11.96 Found: C, 71.53; H, 7.03; N, 11.84 | 164–165 |
| 30 | 6-[4-(2-Chloro-phenyl)-piperazin-1-ylmethyl]-4H-benzo[1,4]oxazin-3-one | $C_{19}H_{20}ClN_3O_2$ Calculated: C, 63.77; H, 5.63; N, 11.74 Found: C, 63.45; H, 5.59; N, 11.67 | 188–189 |
| 31 | 6-[4-(4-Trifluoromethyl-phenyl)-piperazin-1-ylmethyl]-4H-benzo[1,4]oxazin-3-one | $C_{20}H_{20}F_3N_3O_2$ Calculated: C, 61.38; H, 5.15; N, 10.74 Found: C, 61.31; H, 5.31, N, 10.64 | 220 |
| 32 | 6-[4-(4-Chloro-phenyl)-piperazin-1-ylmethyl]-4H-benzo[1,4]oxazin-3-one | $C_{19}H_{20}ClN_3O_2 \cdot 0.5H_2O$ Calculated: C, 62.20; H, 5.77; N, 11.46 Found: C, 62.50; H, 5.81; N, 11.29 | 250–251.5 |
| 33 | 7-[4-(5-Methyl-pyridin-2-yl)-piperazin-1-ylmethyl]-4H-benzo[1,4]oxazin-3-one | $C_{19}H_{22}N_4O_2$ Calculated: C, 67.44; H, 6.55; N, 16.56 Found: C, 67.35; H, 6.60; N, 16.40 | 215 |
| 34 | 7-[4-(4-Methoxy-phenyl)-piperazin-1-ylmethyl]-4H-benzo[1,4]oxazin-3-one | $C_{20}H_{23}N_3O_3$ Calculated: C, 67.97; H, 6.56; N, 11.89 Found: C, 67.72; H, 6.46; N, 11.7 | 235 |
| 35 | 7-[4-(4-Chloro-phenyl)-piperazin-1-ylmethyl]-4H-benzo[1,4]oxazin-3-one | $C_{19}H_{20}ClN_3O_2$ Calculated: C, 63.77; H, 5.63; N, 11.74 Found: C, 62.55; H, 5.54; N, 11.42 | 232–233 |
| 36 | 7-[4-(3,4-Dimethyl-phenyl)-piperidin-1-ylmethyl]-4H-benzo[1,4]oxazin-3-one | $C_{22}H_{26}N_2O_2$ Calculated: C, 75.40; H, 7.48; N, 7.99 Found: C, 75.17; H, 7.25; N, 7.84 | 192–194 |
| 37 | 6-[4-(4-Methoxy-phenyl)-piperidin-1-ylmethyl]-4H-benzo[1,4]oxazin-3-one | $C_{21}H_{24}N_2O_3$ Calculated: C, 71.50; H, 6.86; N, 7.95 Found: C, 71.14; H, 6.62; N, 7.60 | 177–178 |

| Example Number | Compound Name | Elemental Analysis | Melting Point °C. |
|---|---|---|---|
| 38 | 7-[4-(4-Methoxy-phenyl)-piperidin-1-ylmethyl]-4H-benzo[1,4]oxazin-3-one | $C_{21}H_{24}N_2O_3$<br>Calculated: C, 71.57; H, 6.86; N, 7.95<br>Found: C, 71.29; H, 6.83; N, 7.75 | 198–199 |
| 39 | 7-(4-Phenyl-piperidin-1-ylmethyl)-4H-benzo[1,4]oxazin-3-one | $C_{20}H_{22}N_2O_2$<br>Calculated: C, 74.51; H, 6.88; N, 8.62<br>Found: C, 74.59; H, 6.74; N, 8.69 | 184–186 |
| 40 | 7-(4-Naphthalen-2-yl-piperazin-1-ylmethyl)-4H-benzo[1,4]oxazin-3-one | $C_{23}H_{23}N_3O_2$<br>Calculated: C, 73.97; H, 6.21; N, 11.25<br>Found: C, 73.62; H, 6.07; N, 11.40 | 247–249 |
| 41 | 7-(4-p-Tolyl-piperidin-1-ylmethyl)-4H-benzo[1,4]oxazin-3-one | $C_{21}H_{24}N_2O_2$<br>Calculated: C, 74.97; H, 7.19; N, 8.33<br>Found: C, 74.61; H, 7.00; N, 8.55 | 186–188 |

BIOLOGICAL METHODS

Cell Lines Expressing Dopamine Receptor Isoforms

A cell line expressing human dopamine D2 (Long form) receptors was purchased from Oregon Health Sciences University, Portland, Oreg. The D2 receptor cDNA was subcloned into an expression vector, pRc/CMV. The plasmids were transfected by electroporation into CHO K1 cells. A single stable transfectant, resistant to the antibiotic G418, was isolated and selected for use in the binding studies. For D4 binding, CHO K1 cells stably transfected to express the human recombinant dopamine D4.2 receptor subtype, as described by Shih, et al., "The expression and functional characterization of human dopamine D4.2 receptor in CHO K1 cells," *Soc. Neurosci.*, 1995;21(Part 1):621.

Cell Culture and Preparation of Cell Membranes

CHO K1 cells expressing either human D2 and D4.2 receptors were grown in 162 cm² culture flasks in F12 medium (Gibco Laboratories, Grand Island, N.Y.) supplemented with 10% fetal bovine serum (FBS, Hyclone, Logan, Utah) in an atmosphere of 5% $CO_2$/95% air at 37° C. Cells were grown until confluent, after which growth medium was removed and replaced with 0.02% ethylene diamine tetracetate (EDTA) in a phosphate-buffered saline solution (Sigma Chemical Co., St. Louis, Mo.) and scraped from the flasks. The cells were centrifuged at about 1000× g for 10 minutes at 40° C. and then resuspended in TEM buffer (25 mM Tris-HCl, pH 7.4, 5 mM EDTA, and 6 mM $MgCl_2$) for D2 or the D4.2 buffer (50 mM Tris-HCl, pH 7.4, 5 mM EDTA, 1.5 mM $CaCl_2$, 5 mM KCl, and 120 mM NaCl) and homogenized. The membranes were pelleted by centrifugation at 20,000× g at 40° C. for 20 minutes. Then the pellets were resuspended in appropriate buffer at 1 mL/flask and stored at −70° C. until used in the receptor binding assay.

Receptor Binding Assays: D2, D4, 2 Dopamine Receptors

A cell membrane preparation (400 μL) was incubated in triplicate with 50 μL [³H]spiperone (0.2 nM for D2, 0.2 nM for D4.2), 50 μL buffer, or competing drugs where appropriate to give a final volume of 0.5 mL. After 60 minutes incubation at 25° C., the incubations were terminated by rapid filtration through Whatmann GF/B glass fibre filters (soaked for 1 hour in 0.5% polyethylenimine) on a -cell harvester, with three washes of 1 mL ice-cold buffer. Individual filter disks containing the bound ligand were placed in counting vials with 4 mL of scintillation fluid (Ready Gel, Beckman Instrument Inc., Fullerton, Calif.) and then counted in a Beckman LS-6800 liquid scintillation counter at an efficiency of 45%. Nonspecific binding was defined in presence of 1 mM of haloperidol.

Data Calculation

Saturation and competition binding data were analyzed using an iterative nonlinear least-square curve-fitting Ligand program. In competition experiments, apparent $K_i$ values were calculated from $IC_{50}$ values by method of Cheng and Prusoff, "Relationship between the inhibition constant ($K_i$) and the concentration of inhibitor which causes 50% inhibition ($IC_{50}$) of an enzymatic reaction," *Biochem. Pharmacol*, 1973;22:3099–3108. Experimental compounds were made up as stock solutions in dimethyl sulfoxide (DMSO). The final concentration of 0.1% DMSO used in the incubation mixture had no effect on the specific binding. Each observation was carried out in triplicate. To allow these calculations, $K_i$ values were measured for the interaction of various ligands with the receptor. These were: [³H]spiperone binding, human D2, 0.116+0.01 and human D4.2, 0.093+0.005 nM (n=3). The test results are presented below.

| | BINDING DATA | | |
|---|---|---|---|
| Example Number | D2 (Ki, nM) | D4 (Ki, nM) | D2/D4 Ratio |
| 1 | 493 | 4.36 | 113.1 |
| 3 | | 1665 | |
| 4 | >5882 | 23.56 | 249.7 |
| 5 | 2341 | 5.18 | 451.9 |
| 8 | 2196 | 18.3 | 120 |
| 12 | 2983 | 10.66 | 279.8 |
| 13 | 129 | 6.09 | 21.2 |
| 14 | 346 | 6.94 | 49.9 |
| 15 | >5882 | 7.17 | 820.4 |
| 16 | 52.50 | 2.84 | 18.5 |
| 17 | 572 | 1.81 | 316 |
| 18 | | 125.88 | |
| 19 | | 33.30 | |
| 20 | >5882 | 10.77 | 546.1 |
| 21 | 4325 | 17.83 | 242.6 |
| 22 | 3887 | 15.41 | 252.2 |
| 23 | 2616 | 19.01 | 137.6 |
| 24 | 435 | 6.06 | 71.8 |
| 25 | 5592 | 12.34 | 453.2 |
| 26 | 127 | 8.84 | 14.4 |
| 27 | 2616 | 15.61 | 167.6 |
| 28 | 3582 | 15.66 | 228.7 |
| 29 | 1434 | 12.12 | 118.3 |
| 30 | 72 | 13.03 | 5.5 |
| 31 | | 173 | |
| 32 | >5882.4 | 62.47 | 94.2 |
| 33 | 1753 | 1.66 | 1056 |
| 34 | 5882.40 | 5.0 | 1176.5 |
| 35 | 620 | 4.68 | 132.5 |
| 36 | 610 | 2.61 | 233.7 |
| 37 | 698 | 3.87 | 180.4 |
| 38 | 1126 | 6.70 | 168.1 |
| 39 | 68.98 | 7.58 | 9.1 |
| 40 | 673.92 | 13.85 | 48.7 |
| 41 | 287.31 | 2.60 | 110.5 |

What is claimed is:

1. A compound having the Formula I or II

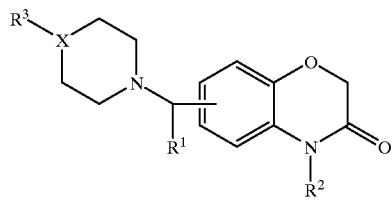

I

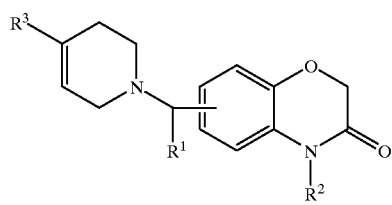

II wherein $R^1$ and $R^2$ are independently hydrogen or $C_1$–$C_6$ alkyl;

X is N or CH; and $R^3$ is phenyl, naphthyl, thiazolyl, thiophene, pyridyl, pyrimidyl, quinolinyl, isoquinolinyl, and imidazolyl, wherein said groups are unsubstituted or substituted by one or two groups, independently selected from halogen, hydroxy, $C_1$–$C_6$ alkoxy, $C_1$–$C_6$ alkyl, —CN, —CF$_3$, or SO$_2$NR$^a$R$^b$ where $R^a$ and $R^b$ are independently hydrogen or $C_{1-6}$ alkyl, and the pharmaceutically acceptable salts thereof.

2. A compound of claim 1 wherein the group

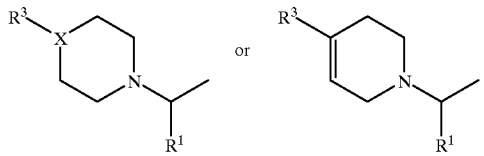

is attached to the benzoxazinone group at the 6 or 7 position.

3. A compound of claim 1 wherein $R^1$ and $R^2$ are hydrogen.

4. A compound of claim 1 wherein $R^3$ is phenyl, halophenyl, methyltolyl, tolyl or SO$_2$NH$_2$.

5. A compound of claim 1 wherein X is N.

6. A compound having the Formula III,

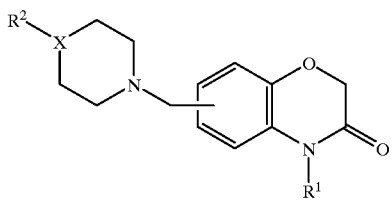

III wherein X is N or CH; $R^1$ is hydrogen or methyl; and
$R^2$ is phenyl or phenyl substituted with one or two groups selected from halo $C_1$–$C_6$ alkyl or SO$_2$NR$^a$R$^b$ where $R^a$ and $R^b$ are independently hydrogen or $C_1$–$C_6$ alkyl, and the pharmaceutically acceptable salts thereof.

7. A compound of claim 6 wherein the group,

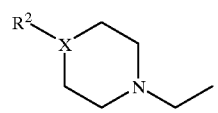

is attached to the benzoxazinone ring at the 6 or 7 position.

8. A compound of claim 6 wherein $R^1$ and $R^2$ are hydrogen.

9. A compound of claim 6 wherein $R^2$ is phenyl halophenyl, methyltolyl, tolyl, or SO$_2$NH$_2$.

10. A compound of claim 1 wherein the compound is

4-[4-(3-oxo-3,4-dihydro-2H-benzo[1,4]oxazin-6-ylmethyl)-piperazin-1-yl]-benzenesulfonamide;

6-[4-(3,4-dimethyl-phenyl)-piperazin-1-ylmethyl]-4H-benzo[1,4]oxazin-3-one;

6-(4-p-tolyl-piperazin-1-ylmethyl)-4H-benzo[1,4]oxazin-3-one;

6-[4-phenyl-piperazin-1-ylmethyl]-4H-benzo[1,4]oxazin-3-one;

7-(4-p-tolyl-piperazin-1-ylmethyl)-4H-benzo [1,4]oxazin-3-one;

7-(4-phenyl-piperazin-1-ylmethyl)-4H-benzo[1,4]oxazine-3-one;

7-[4-(3,4-dimethyl-phenyl)-piperazin-1-ylmethyl]-4H-benzo[1,4]oxazine-3-one;

6-[4-(5-methyl-pyridin-2-yl)-piperazin-1-ylmethyl)-4H-benzo[1,4]oxazin-3-one;

6-(4-p-tolyl-piperidin-1-ylmethyl)-4H-benxo[1,4]oxazin-3-one;

6-[4-(3,4-Dimethyl-phenyl)-piperidin-1-ylmethyl]-4H-benzo[1,4]oxazin-3-one;

6-(4-thiazol-2-yl-piperazin-1-ylmethyl)-4H-benzo[1,4]oxazin-3-one;

6-(4-benzothiazol-2-yl-piperazin-1-ylmethyl)-4H-benzo [1,4]oxazin-3-one;

6-(4-(4,5-dimethyl-thiazol-2-yl)-piperazin-1-ylmethyl]-4H-benzo[1,4]oxazin-3-one;

6-(4-naphthalen-2-yl-piperazin-1-ylmethyl)-4H-benzo[1,4]oxazin-3-one;

6-14-(3-chloro-phenyl)-piperazin-1-ylmethyl]-4H-benzo [1,4]oxazin-3-one;

6-[4-(3,4-dichloro-phenyl)-piperazin-1-ylmethyl]-4H-benzo[1,4]oxazin-3 -one;

2-[4-(3-oxo-3,4-dihydro-2H-benzo[1,4]oxazin-6-ylmethyl)-piperazin-1-yl]-benzonitrile;

6-[4-(4-methoxy-phenyl)-piperazin-1-ylmethyl]-4H-benzo[1,4]oxazin-3-one; or

6-[4-(2-chloro-4-methyl-phenyl)-piperazin-1-ylmethyl]-4H-benzo[1,4]oxazin-3-one.

11. A compound of claim 1 wherein the compound is

6-[4-(4-Fluoro-phenyl)-piperazin-1-ylmethyl]-4H-benzo [1,4]oxazin-3-one;

6-[4-(3-Trifluoromethyl-phenyl)-piperazin-1-ylmethyl]-4H-benzo[1,4]oxazin-3-one;

6-[4-(3,5-Dimethyl-phenyl)-piperazin-1-ylmethyl]-4H-benzo[1,4]oxazin-3-one;

6-[4-(2-Chloro-phenyl)-piperazin-1-ylmethyl]-4H-benzo [1,4]oxazin-3-one;

6-[4-(4-Trifluoromethyl-phenyl)-piperazin-1-ylmethyl]-4H-benzo[1,4]oxazin-3-one;

6-[4-(4-Chloro-phenyl)-piperazin-1-ylmethyl]-4H-benzo[1,4]oxazin-3-one;

7-[4-(5-Methyl-pyridin-2-yl)-piperazin-1-ylmethyl]-4H-benzo[1,4]oxazin-3-one;

7-[4-(4-Methoxy-phenyl)-piperazin-1-ylmethyl]-4H-benzo[4]oxazin-3-one;

7-[4-(4-Chloro-phenyl)-piperzin-1-ylmethyl]-4H-benzo[1,4]oxazin-3-one;

7-[4-(3,4-Dimethyl-phenyl)-piperidin-1-ylmethyl]-4H-benzo[1,4]oxazin-3-one;

6-[4-(4-Methoxy-phenyl)-piperidin-1-ylmethyl]-4H-benzo[1,4]oxazin-3-one;

7-[4-(4-Methoxy-phenyl)-piperidin-1-ylmethyl]-4H-benzo[1,4]oxazin-3-one;

7-(4-Phenyl-piperidin-1-ylmethyl-4H-benzo[1,4]-oxazin-3-one;

7-(4-Naphthalen-2-yl-piperazin-1-ylmethyl)-4H-benzo[1,4]oxazin-3-one; and 7-(4-p-Tolyl-piperidin-1-ylmethyl)-4H-benzo[1,4]oxazin-3-one.

12. A method of treating psychosis, the method comprising administering to a patient suffering therefrom a therapeutically effective amount of a compound of claim 1.

13. A method of treating psychosis, the method comprising administering to a patient suffering therefrom a therapeutically effective amount of a compound of claim 6.

14. A method of treating schizophrenia, the method comprising administering to a patient suffering therefrom a therapeutically effective amount of a compound of claim 1.

15. A method of treating schizophrenia, the method comprising administering to a patient suffering therefrom a therapeutically effective amount of a compound of claim 6.

16. A pharmaceutically acceptable composition that comprises a compound of claim 1 admixed with a pharmaceutically acceptable carrier, excipient or diluent therefor.

17. A pharmaceutically acceptable composition that comprises a compound of claim 6 admixed with a pharmaceutically acceptable carrier, excipient or diluent therefor.

18. The compound 6-[4-(4-chloro-phenyl)-piperazin-1-ylmethyl]-4H-benzo[1,4]oxazin-3-one or pharmaceutically acceptable salt thereof.

19. A pharmaceutical composition comprising 6-[4-(4-chloro-phenyl)-piperazin-1-ylmethyl]-4H-benzo[1,4]oxazin-3-one admixed with a pharmaceutically acceptable carrier, diluent or excipient therefor.

20. A method of treating psychosis comprising administering to a patient suffering therefrom a therapeutically effective amount of 6-[4-(4-chloro-phenyl)-piperazin-1-ylmethyl]-4H-benzo[1,4]oxazin-3-one.

21. A method of treating schizophrenia comprising administering to a patient suffering therefrom a therapeutically effective amount of 6-[4-(4-chloro-phenyl)-piperazin-1-ylmethyl]-4H-benzo[1,4]oxazin-3-one.

* * * * *